United States Patent [19]
Lois

[11] Patent Number: 5,851,232
[45] Date of Patent: Dec. 22, 1998

[54] VENOUS STENT

[76] Inventor: William A. Lois, 2233 E. 65th St., Brooklyn, N.Y. 11234

[21] Appl. No.: 820,639

[22] Filed: Mar. 15, 1997

[51] Int. Cl.$^6$ ........................................................ A61F 2/06
[52] U.S. Cl. ................................................ 623/1; 623/12
[58] Field of Search ................................... 623/1, 11, 12; 606/191, 194, 195, 198

[56] References Cited

U.S. PATENT DOCUMENTS

| | | | |
|---|---|---|---|
| 5,123,917 | 6/1992 | Lee ................................................ | 623/1 |
| 5,282,860 | 2/1994 | Matsuno et al. ............................. | 623/1 |
| 5,354,309 | 10/1994 | Schnepp-Pesch et al. ................. | 623/1 |
| 5,383,926 | 1/1995 | Lock et al. .................................... | 623/1 |
| 5,421,995 | 6/1995 | Lau et al. . | |
| 5,500,014 | 3/1996 | Quijano et al. .............................. | 623/1 |
| 5,549,662 | 8/1996 | Fordenbacher . | |
| 5,562,641 | 10/1996 | Flomenblit et al. . | |
| 5,562,697 | 10/1996 | Christiansen . | |
| 5,607,445 | 3/1997 | Summers .................................... | 623/1 |
| 5,632,771 | 5/1997 | Boatman et al. ............................ | 623/1 |

*Primary Examiner*—Debra S. Brittingham
*Attorney, Agent, or Firm*—Michael I. Kroll

[57] ABSTRACT

A stent assembly (10) for placement in a body lumen (12) acting to retain the body lumen (12) in an open position. The stent assembly (10) includes a cylindrical shell (14) and a plurality of circular coils (16) embedded within the cylindrical shell (14). The stent assembly (14) is changeable between a first unexpanded state for placement within the body lumen (12) and a second expanded state for holding the body lumen (12) open once positioned therein. The cylindrical shell (14) is made of expandable PTFE material and the plurality of coils (16) are formed of cut rings, the cuts in each coil being staggered about the 360 degree radius of the cylindrical shell (14) providing full support for the cylindrical shell (14) throughout its circumference. The cylindrical shell (14) may also include ridges (24) extending from an outer wall (30) thereof for engaging the inner wall (28) and holding the stent assembly (10) in place. This stent assembly (10) is particularly useful as a venous stent due to its physical characteristics.

17 Claims, 2 Drawing Sheets

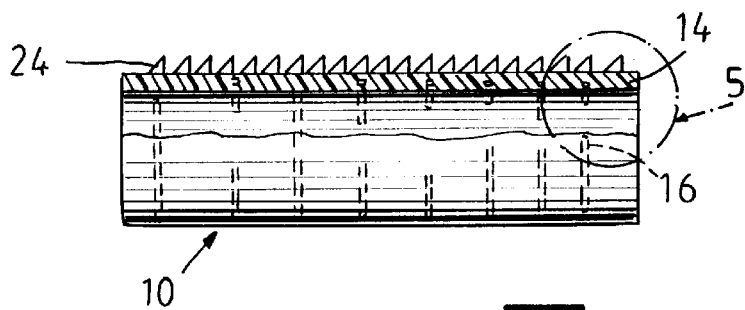
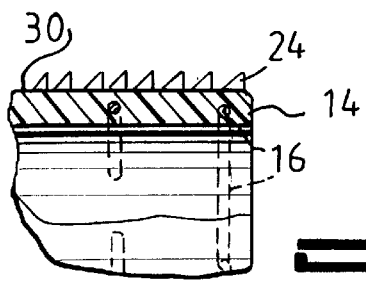
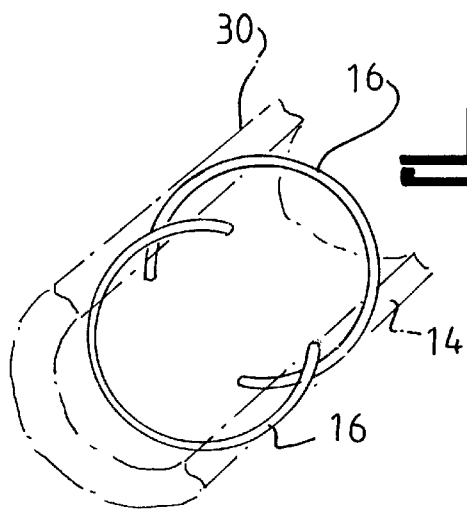
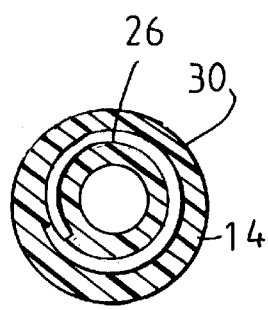

VENOUS STENT

BACKGROUND OF THE INVENTION

1. Field of the Invention

The instant invention relates generally to medical devices and, more specifically, to a stent assembly which may be safely placed in a body lumen thereby preventing the narrowing of the of the lumen's diameter.

1. Description of the Prior Art

Numerous stents have been provided in the prior art For example, U.S. Pat. Nos. 5,421,955; 5,549,662; 5,562,641; and 5,562,697 are all illustrative of such prior art While these units may be suitable for the particular purpose to which they address, they would not be as suitable for the purposes of the present invention as heretofore described.

U.S. Pat. No. 5,421,955 issued on Jun. 6, 1995 to Lipip Lau et al is directed to an expandable stent for implantation in a body lumen, such as an artery, and a method for making it from a single length of tubing. The stent consists of a plurality of radially expandable cylindrical elements generally aligned on a common axis and interconnected by one or more interconnective elements. The individual radially expandable cylindrical elements consist of ribbon-like material disposed in an undulating pattern. The stents are made by coating a length of tubing with an etchant-resistive material and then selectively removing portions of the coating to form a pattern for the stent on the tubing and to expose the portions of the tubing to be removed. This may be done by machine-controlled activation and relative positioning of a laser in conjunction with the coated tubing. After the patterning of the tubing, the stent is formed by removing exposed portions of the tubing by an etching process.

U.S. Pat. No. 5,549,662, issued Aug. 27, 1996 to Paul J. Fordenbacher provides a lumen support device, or a stent, used to open or expand a body lumen. The stent incorporates elongated parallel stent components with circumferential members, fingers, which weave into paired slots of an adjacent stent component This weave-like interlocking configuration enables the stent to expand radially without yielding or plastically deforming the material of which the stent is fabricated. The weave-like mechanism allows for uniform, smooth expansion without change in longitudinal dimensions of the complete assembly. Once assembled, the plurality of parallel elongated stent components form a cylindrical configuration. The invention provides a stent able to support body lumens and adapt to curves or irregularities in body lumens without losing its formation or its longitudinal dimensions. It is designed to permit flexing both radially and longitudinally to conform to the curved body of the applicable lumen. The device is delivered using a percutaneous transluminal catheter device which may incorporate an inflatable balloon, self-expanding material or both to expand the stent.

U.S. Pat. No. 5,562,641, issued Oct. 8, 1996 to Josef Flomenblit et al. discloses a stent for placing in a tubular organ so as to support its diameter to remain above a critical diameter. The stent comprises a spiral coil or cylinder made of a two-way shape memory alloy and has a super-elastic state in which the stent's diameter is at least about the critical diameter or more but within a physiological range tolerated by the organ and having a soft state in which the stent's diameter, after changing to this state from the super-elastic state, which is less than the critical diameter. The shape memory alloy has two transition temperatures being within a range that will not damage biological tissue, of which a first transition temperature is a temperature in which it changes from the soft state to the super-elastic state and of which a second transition temperature is a temperature in which it changes from the super-elastic state to the soft state. The arrangement being such that after changing into one of the two states, the stent remains in that state at body temperature.

U.S. Pat. No. 5,562,697, issued Oct. 8, 1996 to Frank K. Christiansen discloses a self-expanding stent assembly and methods for the manufacture thereof and for introduction of such stent assembly into a body passage or duct of a patient. A self-expanding endovascular stent assembly comprises at least one stent segment formed by a single piece of wire arranged in a closed zig-zag configuration with struts joining each other joints and a covering sleeve. The stent segment is compressible from an expanded condition with a first radius into an introduction condition with second radius. The struts are retained solely by the sleeve, which is relatively inelastic and has a thickness of not more than 1 percent of the first radius.

BRIEF SUMMARY OF THE INVENTION

The present invention is concerned with medical devices for placement in a body lumen such as arteries and veins and, more specifically, to a stent assembly which may be safely placed in a body lumen thereby preventing the narrowing of the of the lumen's diameter.

A primary object of the present invention is to provide a stent assembly able to effectively prevent the narrowing of the body lumen in which it is placed.

Another object of the present invention is to provide a stent assembly able to be easily inserted into the body lumen.

An additional object of the present invention is to provide a stent assembly able to be easily deployed for use once inserted within the lumen.

Another object of the present invention is to provide a stent assembly able to provide a constant pressure on the walls of the lumen in its expanded state.

A further object of the present invention is to provide a stent assembly having a flexible body able to hold the lumen open while maintaining the compliance of the lumen.

A still further object of the present invention is to provide a stent assembly having a smooth adherent surface, preventing fatty deposits and oils from sticking thereto.

An even further object of the present invention is to provide a stent assembly able to retain its position within the lumen without causing damage to the lumen.

A yet further object of the present invention is provide a stent assembly having a structure flexible and delicate enough to be placed in a vein without damaging the vein.

A stent assembly for placement in a body lumen acting to retain the body lumen in an open position. The stent assembly includes a cylindrical shell and a plurality of circular coils embedded within the cylindrical shell. The stent assembly is changeable between a first unexpanded state for placement within the body lumen and a second expanded state for holding the body lumen open once positioned therein. The cylindrical shell is made of expandable PTFE material and the coils are formed of cut rings, the coils being positioned so that the cuts in the coils are staggered about the 360 degree radius of the cylindrical shell. When the stent assembly is in the second expanded state the staggering of the cuts in the coils provides full support for the shell throughout its circumference. The cylindrical shell may also include ridges extending therefrom for engaging the lumen wall and holding the stent assembly in place. This stent assembly is particularly useful as a venous stent due to its physical characteristics.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 4 is a cross-sectional view of the stent assembly of the present invention including ridges for retaining the stent assembly within the lumen;

FIG. 5 is an exploded cross-sectional view of a portion of the stent assembly of the present invention within the circle labeled 5 in FIG. 4;

FIG. 6 is a perspective view of the coils of the stent assembly of the present invention in its expanded state; and FIG. 7 is a cross-sectional view of the stent assembly of the present invention in the unexpanded state.

DESCRIPTION OF THE REFERENCED NUMERALS

Figure 1:
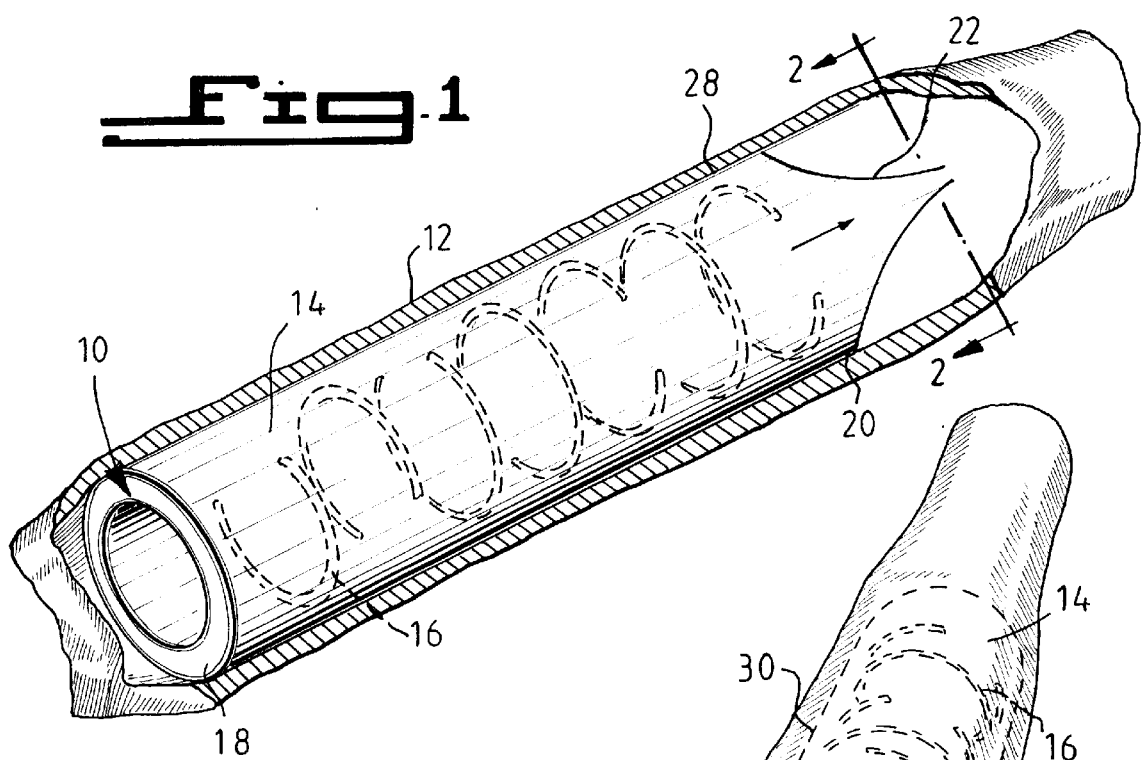
FIG. 1 is a cross-sectional view of the stent assembly of the present invention positioned within a body lumen.

Turning now descriptively to the drawings, in which similar reference characters denote similar elements throughout the several views, the Figures illustrate an electronic ballast circuit of the present invention. With regard to the reference numerals used, the following numbering is used throughout the various drawing figures.

10 stent assembly of the present invention in an expanded state
12 body lumen
14 cylindrical shell
16 plurality of coils
18 first edge of cylindrical shell
20 second edge of cylindrical shell
22 valve device
24 ridges
26 coil in unexpanded state
28 inner wall of body lumen
30 outer wall of cylindrical shell

DETAILED DESCRIPTION OF THE PREFERRED EMBODIMENT

Referring now to FIGS. 1–7, a preferred embodiment of the stent assembly of the present invention is illustrated.

Specifically, FIG. 1 shows the stent assembly indicated generally by the numeral 10. The stent assembly 10 is positioned within a body lumen 12, e.g. a vein or artery, and includes an outer shell 14. Embedded within the outer shell 14 are a plurality of coils 16. Each of the plurality of coils 16 are in the form of cut rings extending through slightly more than one complete 360 degree turn in an at rest unexpanded state. The number of coils 16 embedded within the shell 14 may vary and is determined by the length of the stent assembly 10 needed.

The outer shell 14 is cylindrical in shape and has a thickness greater than the thickness of each of the plurality of coils 16. The cylindrical shell 14 is preferably formed of polytetrafluoroethelene also known as PTFE material or teflon®. This material is a compound of flourine and ethylene having an adherent surface preventing fats and oils from bonding thereto and thus, preventing clogging of the stent assembly 10. Furthermore, this material has a slippery surface and is substantially insulated from chemical attack. Thus, bodily fluids and substances traveling with the fluids passing through the cylindrical shell 14 will neither stick to nor harm the stent assembly. PTFE material is also flexible, can be expanded to fit snugly within the body lumen 12 and is able to bend with the body lumen 12 thus maintaining the compliance of the body lumen 12.

While a preferred material for the cylindrical shell 14 is shown and described herein, those of ordinary skill in the art who have read this description will appreciate that there are numerous other materials for the cylindrical shell 14 and, therefore, the cylindrical shell 14 should be construed as including all such materials as long as they are able to produce the desired result of housing a plurality of coils 16 and forming to the shape of a body lumen 12, and therefore, that all such alternative materials are to be considered as equivalent to the one described herein.

As is illustrated in FIG. 1, the coils 16 are embedded within the cylindrical shell 14 and positioned such that each coil is separated from adjacent coils by a distance of approximately 2–3 mm. on either side. The plurality of coils 16 are spaced throughout the length of the cylindrical shell 14 wherein coils 16 positioned adjacent the edges 18 and 20 of the cylindrical shell 14 are separated from its respective edge by a distance of approximately 1 mm.

FIG. 1 also shows an valve 22 for regulating the flow of bodily fluid through the stent assembly 10. The valve 22 is placed on a down stream end of the cylindrical shell 14 at the point where bodily fluid passing therethrough exits the stent assembly 10. Such a valve device 22 is an optional feature and is used in stent assemblies 10 placed within lumens 12 located in lower body extremities.

Figure 2:
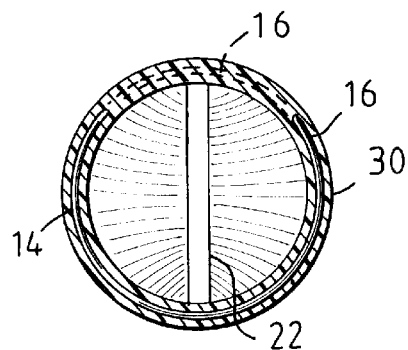
FIG. 2 is a cross-sectional view of the stent assembly of the present invention taken along the line 2—2 of FIG. 1.

FIG. 2 illustrates a cross-sectional view of FIG. 1 taken along the line 2–2 of FIG. 1. This figure clearly illustrates the coils 16 embedded within the cylindrical shell 14. The coils 16 can also be seen from all figures to be oriented to in a staggered fashion to cover a 360 degree rotation about the cylindrical shell 14 thereby providing support to the entire circumference of the cylindrical shell 14 when in an expanded state. Two coils 16 in a staggered fashion are shown in this figure, one in bold outline and the other in dashed lines indicating its depth from the cross-sectional cut. The valve device 22 is also depicted to show the flow of fluid through the valve device 22 and exiting the stent assembly 10.

Figure 3:
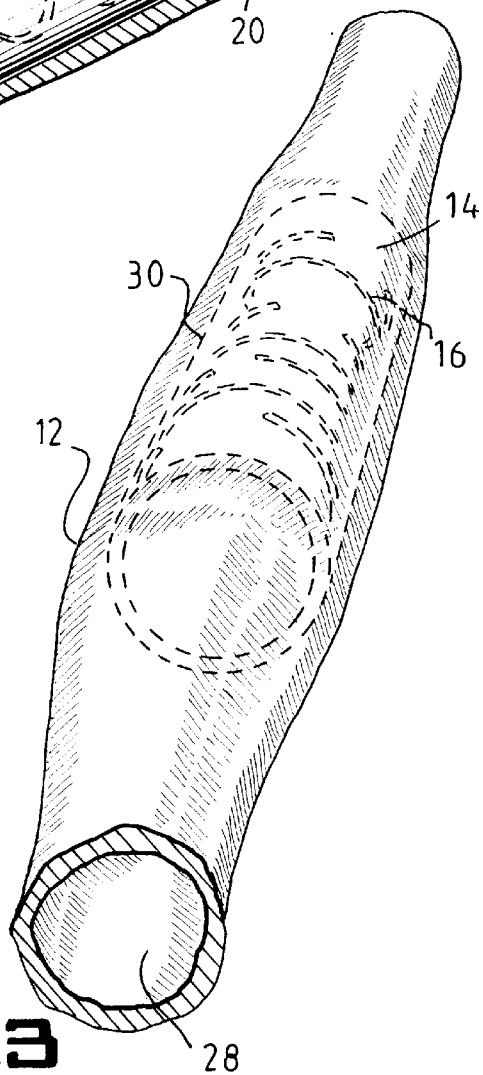
FIG. 3 is a perspective view of a body lumen including the stent assembly assembly of the present invention positioned therein.

FIG. 3 illustrates a body lumen 12 having the stent assembly 10 of the present invention placed therein. As can be seen from the figure, when the stent assembly 10 is in its expanded operational state the body lumen 12 is caused to expand slightly in the area occupied by the stent assembly 10 due to pressure on the inner wall 28 exerted by the cylindrical shell 14 and plurality of coils 16 and providing a passage through the lumen equal in size to the passage prior to insertion of the stent assembly 10.

FIGS. 4 and 5 illustrate the stent assembly of the present invention including a plurality of ridges 24. As the surface of the cylindrical shell 14 is adherent, the stent assembly 10 may migrate out of its intended position once placed within the lumen 12. The outer surface 30 of the cylindrical shell 14 may thus be provided with the plurality of ridges 24 positioned along its length for engaging the inner wall 28 of the lumen 12 and holding the stent assembly 10 in its intended position. The plurality of ridges 24 are rigid enough to secure the stent assembly 10 in place while not causing damage to the inner wall 28 of the lumen 12.

The staggered orientation of the coils 16 is best illustrated by FIG. 6. As can be seen the coils 16 are positioned in a staggered fashion to cover the full 360 degree circumference of the cylindrical shell 14 although individually each coil covers less than a full 360 degrees. By staggering the individual coils 16 in this manner and positioning the plurality of coils 16 along the entire length of the cylindrical shell 14, the stent assembly 10 is strengthened throughout both its entire length and circumference while maintaining its flexibility due to the pliable nature of the PTFE material and spacing of the coils 16.

FIG. 7 illustrates a cross sectional view of the stent assembly in an unexpanded state and ready for insertion into a body lumen 12. In this state, each coil 16 covers greater than a 360 degree turn and the cylindrical shell 14 is substantially smaller in circumference. As is depicted in the figure, the circumference of the cylindrical shell 14 and the cut in the coil causes the free ends of the coil to overlap in the unexpanded state. The smaller circumference of the cylindrical shell in the unexpanded state allows for easy insertion and correct placement of the stent assembly 10 in the lumen 12 as the circumference of the stent assembly 10 must be smaller than the circumference of the lumen 12.

Once the stent assembly 10 is positioned within the lumen 12, the stent assembly 10 is expanded causing the individual coils 16 and thus the cylindrical shell 14 to expand to a greater circumference. When the stent assembly is expanded, the free ends of the coil are caused to separate producing a gap therebetween and forming a substantially C-shaped coil. Thus, although the coils 16 are able to cover a greater area than the 360 degree circumference of the unexpanded cylindrical shell 14, each of the plurality of coils 16 are not long enough to cover the full 360 degree circumference of the expanded cylindrical shell 14. The forming of the gap in each individual coil adds to the flexibility of the stent assembly 10.

Furthermore, as the cylindrical shell 14 is expanded, its material stretches and thus thins to provide the increased circumference necessary to fit securely within the lumen 12. Thus, the thickness of the shell 14 in the unexpanded state is greater than the thickness in the expanded state. When the plurality of coils 16 are embedded in the cylindrical shell 14, the thickness of the cylindrical shell 14 in the expanded state must be considered. If the thickness of the cylindrical shell 14 in the expanded state is less than the thickness of the coils 16 then the stent assembly 10 may fail when expanded within a lumen 12.

In operation, the stent assembly 10 is deployed in the lumen 12 using a standard ballon delivery and deployment system. The catheter and balloon combination is a conventional balloon dilation catheter used in other procedures and forms no part of the present invention, thus no further discussion of its structure is deemed necessary. A delivery catheter including an expandable balloon is used to insert the stent assembly 10 into the lumen 12. The balloon is placed within the cylindrical shell 14 of the stent assembly 10 which is in its unexpanded state. Thus, the plurality of coils are unexpanded and the free ends of each of the coils overlap each other.

Once the cylindrical shell 14 of the stent assembly 10 is mounted onto the balloon of the catheter the balloon may be slightly inflated to snugly secure the stent assembly 10 onto the catheter but not enough to cause expansion of the cylindrical shell 14. The catheter-stent assembly is then introduced within the patient's lumen 12 in a conventional manner and is guided along a guide wire to the damaged section of the lumen 12. At this point, the balloon is expanded and thus the cylindrical shell 14 is also expanded. This forces the plurality of coils 16 to also expand forcing the free ends of each respective coil to separate and to form a substantially C-shaped coil. As the cuts or gaps in the coils are staggered throughout the 360 degree circumference of the cylindrical shell 14, the entire circumference of the cylindrical shell 14 is supported.

In the expanded state the outer wall 30 of the cylindrical shell 14 is in contact with the inner wall 28 of the lumen 12. The ridges 24 on the outer wall 30 of the stent assembly 10 are thus caused to engage the inner wall 28 of the lumen 12 acting to hold the stent assembly 10 securely in position. Body fluid is now allowed to flow through the lumen 12 and stent assembly 10, the stent assembly 10 acting to hold the lumen 12 open.

If the stent assembly 10 is positioned within a lumen 12 in a lower bodily extremity such as a vein or artery in the leg, a valve device 22 may be positioned on the downstream end of the stent assembly 10 prior to deployment in the lumen 12. This valve device 22 will act to regulate the flow of bodily fluids through the stent assembly 10. In this expanded state the cylindrical shell 14 retains its flexibility and thus is able to move with the compliance of the lumen 12.

Based upon the structure and functioning of the stent assembly of the present invention effective prevention of the narrowing of a body lumen is possible. The structure and characteristics of the stent assembly also makes it ideal for use as a venous stent This stent assembly is easily inserted into a body lumen and easily deployed for use once inserted. In its expanded state, the stent assembly exerts a constant pressure on the inner wall of the lumen to engage the lumen with the ridges on the outer wall thereof while maintaining its flexibility thus, it is able to retain its position while sufficiently holding the lumen open and maintaining the compliance of the lumen. Furthermore, the smooth adherent surface prevents fatty deposits and oils from sticking thereto.

It will be understood that each of the elements described above, or two or more together, may also find a useful application in other types of applications differing from the type described above.

While the invention has been illustrated and described as shown in the drawings, it is not intended to be limited to the details shown, since it will be understood that various omissions, modifications, substitutions and changes in the forms and details of the formulation illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by letters patent is set forth in the appended claims:

1. A stent assembly for placement in a body lumen including an inner wall, said stent assembly comprising:
   a) a cylindrical shell including an outer wall; and
   b) a plurality of circular coils embedded within said shell, said assembly being changeable from a first unexpanded state for placement of said stent assembly within the body lumen to a second expanded state in which said outer wall of said cylindrical shell contacts the inner wall of the body lumen and said plurality of coils are each expanded to be substantially C-shaped in form for holding the body lumen open, wherein each of said plurality of coils are formed from cut rings, the cut in each of said plurality of coils forming first and second ends, said first and second ends being separated to form a gap therebetween, said plurality of gaps being staggered to cover a 360 degree rotation about said cylindrical shell when said stent assembly is in said second expanded state.

2. A stent assembly as recited in claim 1, further comprising a plurality of ridges connected to said outer wall for engaging the inner wall of the lumen when said stent assembly is in said second expanded state.

3. A stent assembly as recited in claim 1, wherein said cylindrical shell is made of polytetrafluoroethylene.

4. A stent assembly as recited in claim 1, wherein said plurality of coils are made of a metallic substance.

5. A stent assembly as recited in claim 3, wherein said cylindrical shell has a smooth, adherent surface.

6. A stent assembly as recited in claim 1, further comprising a valve assembly connected to said cylindrical shell for regulating a flow of bodily fluid through said stent assembly.

7. A stent assembly as recited in claim 1, wherein each of said plurality of coils are formed from cut rings, the cut in said plurality of coils producing a first and second free end, said first and second free ends being positioned in an overlapped fashion when said stent assembly is in said first unexpanded state.

8. A stent assembly as recited in claim 1, wherein said cylindrical shell has a length and said plurality of coils are spaced throughout said length, each of said plurality of coils being spaced from adjacent coils by approximately 2–3 mm.

9. A stent assembly as recited in claim 1, wherein said cylindrical shell includes first and second ends and first and second edges, said first and second edges each positioned at a respective one of said first and second ends and first and second coils of said plurality of coils are spaced by approximately 1 mm. from said first and second edges respectively.

10. A stent assembly for placement in a body lumen including an inner wall, said stent assembly comprising:
    a) a cylindrical shell including an outer wall; and
    b) a plurality of circular coils embedded within said cylindrical shell, each of said plurality of coils being formed from a cut ring and including a circumference, a first free end and a second free end, wherein said stent assembly is changeable from a first unexpanded state for placement of said stent assembly within the body lumen wherein said first and second free ends of each coil are positioned in an overlapped manner to a second expanded state in which said outer wall of said cylindrical shell contacts the inner wall of the body lumen, said circumference of each of said plurality of coils is increased and said first and second free ends are separated to form a substantially C-shaped coil for holding the body lumen open, wherein said first and second ends form a gap therebetween when said stent assembly is in said second expanded state, said plurality of gaps being staggered to cover a 360 degree rotation about said cylindrical shell.

11. A stent assembly as recited in claim 10, further comprising a plurality of ridges connected to said outer wall for engaging the inner wall of the lumen when said stent assembly is in said second expanded state.

12. A stent assembly as recited in claim 10, wherein said cylindrical shell is made of polytetrafluoroethylene.

13. A stent assembly as recited in claim 12, wherein said cylindrical shell has a smooth, adherent surface.

14. A stent assembly as recited in claim 10, wherein said plurality of coils are made of a metallic substance.

15. A stent assembly as recited in claim 10, further comprising a valve assembly connected to said cylindrical shell for regulating a flow of bodily fluid through said stent assembly.

16. A stent assembly as recited in claim 10, wherein said cylindrical shell has a length and said plurality of coils are spaced throughout said length, each of said plurality of coils being spaced from adjacent coils by approximately 2–3 mm.

17. A stent assembly as recited in claim 10, wherein said cylindrical shell includes first and second ends and first and second edges, said first and second edges each positioned at a respective one of said first and second ends and first and second coils of said plurality of coils are spaced by approximately 1 mm. from said first and second edges respectively.

* * * * *